United States Patent [19]

Hamers et al.

[11] Patent Number: 5,568,810
[45] Date of Patent: Oct. 29, 1996

[54] ULTRASOUND COUPLING MEDIUM WARMER AND STORAGE MEANS

[75] Inventors: Timothy F. Hamers, Windlake; Lawrence E. Murphy, Shorewood; Wayne R. Vohnoutka, Waukesha, all of Wis.

[73] Assignee: General Electric Company, Milwaukee, Wis.

[21] Appl. No.: 563,414

[22] Filed: Nov. 28, 1995

[51] Int. Cl.⁶ .................................................. A61B 8/00
[52] U.S. Cl. ................................. 128/660.01; 128/898
[58] Field of Search ......................... 128/660.01, 662.02, 128/662.03, 663.01; 73/898, 644

[56] References Cited

U.S. PATENT DOCUMENTS 4,282,880  8/1981  Gardineer et al. ................. 128/660.01
4,844,080  7/1989  Frass et al. ........................ 128/660.01

*Primary Examiner*—George Manuel
*Attorney, Agent, or Firm*—B. Joan Haushalter; John H. Pilarski

[57] ABSTRACT

A container of ultrasound coupling medium, used in conjunction with an ultrasound imaging system, is stored for operator convenience and patient comfort. Initially, at least one location on the ultrasound imaging system is identified, which has a predetermined thermal profile. The container of coupling medium is then stored at any of the identified locations to maintain the coupling medium at a desired temperature.

4 Claims, 2 Drawing Sheets

ULTRASOUND COUPLING MEDIUM WARMER AND STORAGE MEANS

TECHNICAL FIELD

The present invention relates to ultrasound imaging and, more particularly, to a warming location for the coupling medium used in conjunction with ultrasound imaging systems.

BACKGROUND ART

Ultrasonic echoes from deliberately launched diagnostic sound waves into tissue are attenuated in proportion to the distance that the sound waves must travel to reach the reflector, plus the distance that the resulting echoes must travel back to reach the receiver. Since sound waves are attenuated as they pass through the human body, the deeper the penetration, the greater the attenuation.

The ultrasound diagnostic imaging profession uses a substance called a "coupling medium" to enhance transmission of the sound waves between the machine (transducer) and the patient. This medium is most often an aqueous gel. Industry standard containers for this gel are pliable thermoplastic bottles, having a capacity of approximately 0.25 liters. The aqueous gel is applied liberally to the skin area of the patient where the transducer will be in contact.

It is desirable to keep this coupling gel at or near body temperature so that patient discomfort is reduced when the gel is applied to the patient. Most often, the temperature of the coupling medium is raised and maintained through the use of special stand-alone, electrical heating devices. These use their own electrical connection (short cord) to receive power and heat the container of coupling medium to about 35° C. and are usually located on a counter or table in an examination room or clinic.

Unfortunately, this requires the operator to leave the ultrasound machine to get the gel. Consequently, many operators, desiring to keep the gel more readily available, simply keep it on or near the ultrasound equipment. Of course, then the gel is not warming, and the patient has uncomfortably cool gel applied to his or her skin.

In an effort to provide convenience for the operator, numerous locations have been provided for the operator to place the container of coupling gel between applications on patients. However, the problem with many of these locations is that even though the coupling medium is conveniently placed for the sonographer to reach and apply it to the patient, the medium is no longer being maintained at an elevated temperature and must be returned to its special heating device for re-warming.

It would be desirable then to have a convenient, on-the-machine storage location for the coupling medium which raises the temperature of the medium and maintains it at a comfortable level for use.

SUMMARY OF THE INVENTION

The present invention provides both convenience for the sonographer and comfort for the patient by locating convenient and heated storage for the coupling medium used with ultrasound diagnostic imaging systems.

In accordance with one aspect of the present invention, a method for storing an ultrasound coupling medium comprises the steps of identifying at least one location on the ultrasound imaging system which uses latent heat to maintain desired thermal properties; and storing the container at any of the identified latent heat locations. The latent heat locations have the dual advantage of being both convenient for the sonographer to use and comfortable for the patient, in that the coupling medium is maintained at a desired temperature.

Accordingly, it is an object of the present invention to provide a convenient storage location for ultrasound coupling medium substance. It is another object of the present invention to provide the coupling medium in a convenient location, at a temperature which will be comfortable to the patient.

Other objects and advantages of the invention will be apparent from the following description, the accompanying drawings and the appended claims.

DETAILED DESCRIPTION OF THE PREFERRED EMBODIMENTS

The present invention improves ultrasound operator efficiency and convenience, by providing numerous locations for the operator to place a container of coupling substance between applications on patients. The present invention also raises the temperature of the substance and maintains the temperature at a comfortable level for use.

Figure 1:
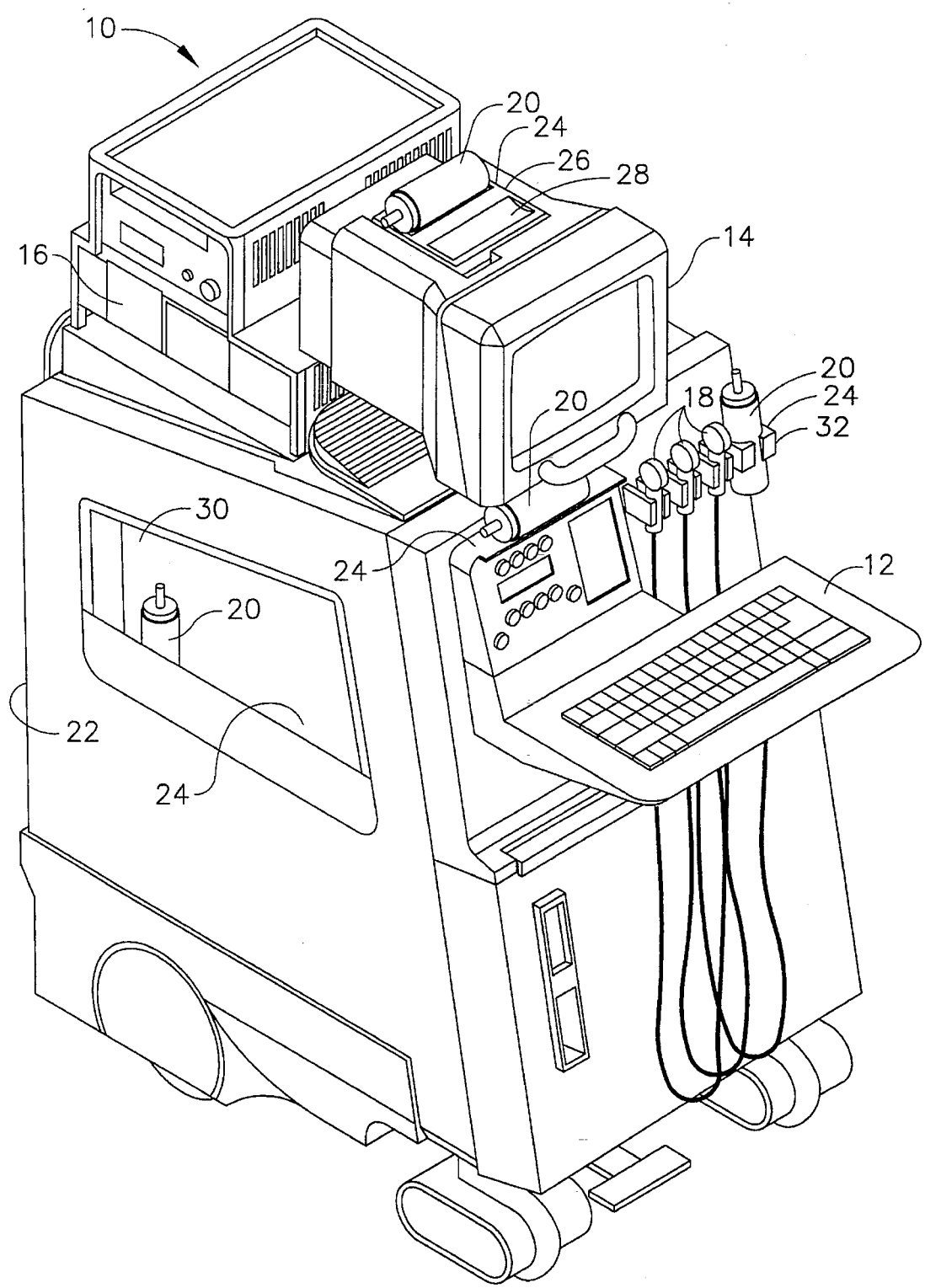
FIG. 1 is a perspective view of an ultrasound machine, illustrating possible latent heat locations for ultrasound imaging coupling medium substances.

Referring now to the drawings, in FIG. 1, the present invention uses latent, i.e., waste, heat generated by an ultrasound imaging system 10 to raise the temperature of the substance and maintain the temperature of the substance at or near body temperature, to minimize patient discomfort. The latent heat comes from the normal function of the electronic components in the machine.

Continuing with FIG. 1, a typical ultrasound imaging system 10 comprises a keyboard 12 for receiving instructions and data from the sonographer, which can be output via a monitor 14 and a printer unit 16. A probe 18 contacts the skin of the patient and is guided over and around the area of interest. A coupling medium, such as a gel, stored in a container 20, is applied to the probe to enhance the workability of the probe. The entire system 10 is typically housed in and on a housing unit 22.

Obviously, since the coupling medium contacts the patient's skin, it is desirable to maintain the coupling medium at a temperature near body temperature. In accordance with the present invention, at least one location, and preferably a plurality of locations 24, on the ultrasound unit 10 are identified which are both convenient for the sonographer and have the proper thermal profile for maintaining the coupling medium at the desired temperature.

Figure 2:
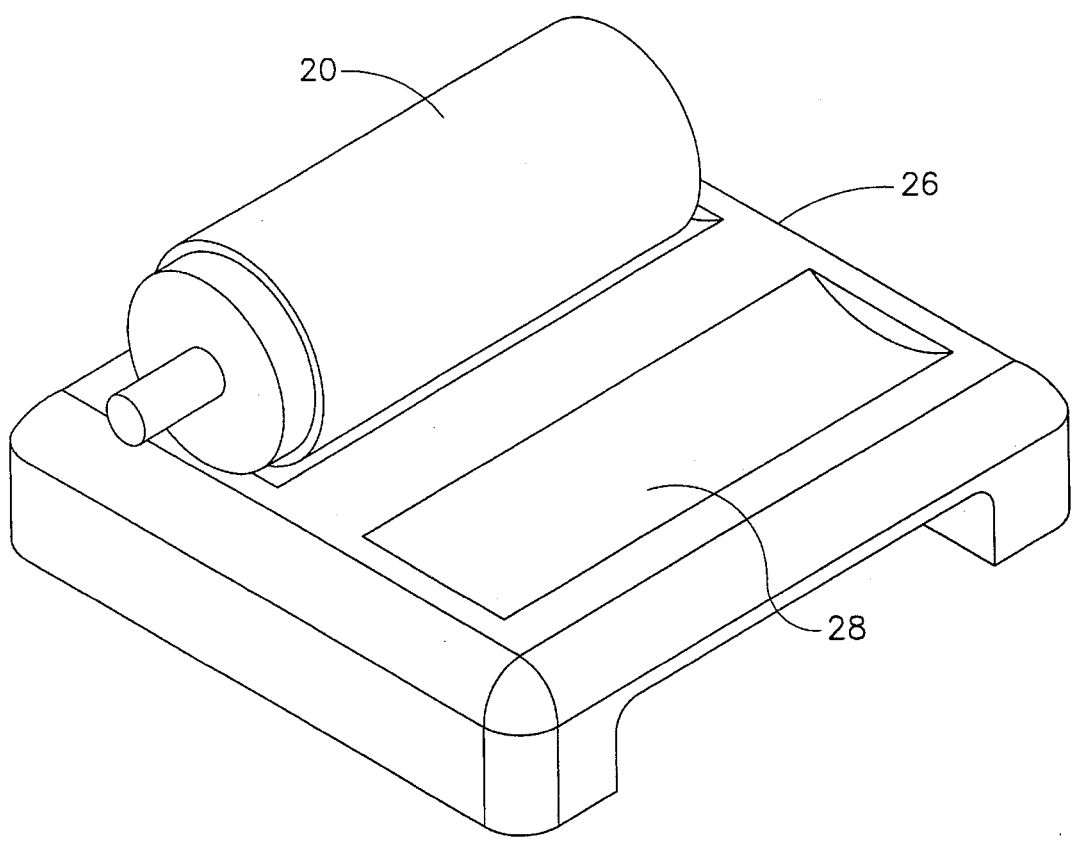
FIG. 2 is a perspective illustration of a removable tray for holding ultrasound imaging coupling medium containers.

In a preferred embodiment of the present invention, the ideal location is on top of the monitor 14. Of course, it will be obvious to those skilled in the art that other locations on and around a given ultrasound machine can be used, as illustrated in FIG. 1. In the preferred embodiment, for convenience and storage, the top of the monitor 14 enclosure comprises a removable tray 26, best illustrated in FIG. 2. The removable tray 26 has a plurality of recesses 28 specifically contoured to hold industry standard containers 20 of coupling medium. The recesses 28 are also contoured, as illustrated in FIG. 2, to maintain the temperature of the container 20 contents during periods of routine operation and use. The tray 26 on the monitor is configured to maintain a steady-state temperature of 35° C. to within ±20°. Since the latent heat of the monitor is used to maintain the temperature, there is no special thermostatic control required. The tray 26 is preferably removable to allow for routine cleaning and/or replacement.

When the location 24 is the top of the monitor, the tray 26 provides a variety of functions. Since the monitor is otherwise flat, the contoured trays are desirable to keep the cylindrical containers from rolling around. The tray is also advantageous because it can be removed for cleaning. Furthermore, the tray is essential to maintain the proper temperature and thermal conditions.

Of course, other suitable locations 24 exist for storing the containers 20, and heating and maintaining the temperature of the container contents. For example, the container could be stored in contoured recesses located under and/or around the monitor 14, as well as on top of the monitor 14. Another location which is both convenient for the sonographer and has the proper thermal profile for maintaining the coupling medium at the desired temperature is often found inside pockets and openings, such as opening 30, in the housing 22. Yet another suitable location for container storage is near the keyboard 12, against the housing 22. A holding means, such as clip 32, may be employed to hold the container 20 in this or other locations. It will also be obvious to those skilled in the art that the addition of vents, ducting, and other heat/air transfer means may be necessary to make certain locations suitable latent heat locations. At locations other than on top of the monitor, the contoured trays 26 may be desirable for ease of cleaning, but are not necessary for maintaining the temperature of the container contents.

One primary difference between the approach of the present invention and other prior art approaches is that there is no other convenient, on-the-machine storage location provision with the capability, of warming and maintaining a temperature for the coupling medium. Another difference is that no supplemental power cord is required accomplish heating and maintaining the coupling medium to and at a desired temperature.

The invention has been described in detail with particular reference to certain preferred embodiments thereof, but it will be understood that modifications and variations can be effected within the spirit and scope of the invention.

We claim:

1. A method for storing a container of ultrasound coupling medium used in conjunction with an ultrasound imaging system having a monitor for visually outputting data to a sonographer, the method comprising the steps of:

identifying at least one location on the ultrasound imaging system having a predetermined thermal profile; and storing the container at the at least one identified location to maintain the coupling medium at a desired temperature.

2. A method for storing a container of ultrasound coupling medium as claimed in claim 1 wherein the at least one location on the ultrasound imaging system comprises a first location on top of the monitor.

3. A method for storing a container of ultrasound coupling medium as claimed in claim 2 wherein the predetermined thermal profile of the first location on top of the monitor heats the coupling medium to a desired temperature and maintains the coupling medium at that desired temperature.

4. A method for storing a container of ultrasound coupling medium as claimed in claim 1 wherein the step of storing the container at the at least one identified location further comprises the step of providing a removable tray for receiving and holding the container.

\* \* \* \* \*

UNITED STATES PATENT AND TRADEMARK OFFICE
CERTIFICATE OF CORRECTION

PATENT NO : 5,568,810
DATED : Oct. 29, 1996
INVENTOR(S): Timothy F. Hamers, et al It is certified that error appears in the above-identified patent and that said Letters Patent is hereby corrected as shown below:

At column 3, line 4, of the Patent, change "$\pm 20°$" to --$\pm 2°$--.

Signed and Sealed this

Second Day of December, 1997

Attest:

BRUCE LEHMAN

Attesting Officer    Commissioner of Patents and Trademarks